United States Patent [19]

Ferruti et al.

[11] Patent Number: 5,631,336
[45] Date of Patent: May 20, 1997

[54] NEW CHAIN-TERMINATED N-VINYL LACTAM POLYMERS AND GRAFT-COPOLYMERS AND METHODS FOR MAKING SAME

[75] Inventors: Paolo Ferruti, Milan; Elisabetta Ranucci, Brescia; Luciana Sartore, Marano Vicentino; Paolo Caliceti, Padova; Oddone Schiavon, Padova; Francesco M. Veronese, Padova, all of Italy

[73] Assignee: Consiglio Nazionale Delle Ricerche, Rome, Italy

[21] Appl. No.: 112,077

[22] Filed: Aug. 26, 1993

[30] Foreign Application Priority Data

Aug. 27, 1992 [IT] Italy .................. MI92A2018

[51] Int. Cl.$^6$ .................. C08F 126/06; C08F 126/10; C08F 2/38
[52] U.S. Cl. .................. 526/264; 526/82; 526/84
[58] Field of Search .................. 526/264, 82, 84

[56] References Cited

U.S. PATENT DOCUMENTS

| | | | |
|---|---|---|---|
| 2,982,762 | 5/1961 | Voeks et al. | 260/88.3 |
| 3,270,032 | 8/1966 | Erner. | |
| 4,057,533 | 11/1977 | Hort et al. | 526/264 |

*Primary Examiner*—Joseph L. Schofer
*Assistant Examiner*—Wu C. Cheng
*Attorney, Agent, or Firm*—Sherman and Shalloway

[57] ABSTRACT

A water-soluble polyvinyl 5-membered lactam having a molecular weight ranging from about 1000 to about 20,000 and chain-terminated with a compound selected from the group consisting of compounds of the following formulas

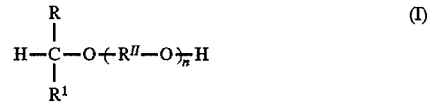

and

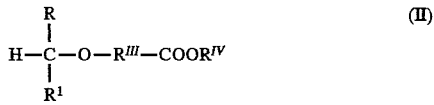

wherein R and $R^1$ are $C_1$ to $C_4$ alkyl or substituted alkyl; n is 0 to 20; $R^{II}$ is ethylene; $R^{III}$ is $C_1$ to $C_{24}$ alkylene or substituted alkylene; and $R^{IV}$ is $C_1$ to $C_4$ alkyl or substituted alkyl; can be prepared by polymerizing an N-vinyl 5-membered lactam in a liquid solvent-chain terminator compound of the formula (I) or (II) in the presence of a free radical initiator. The lactam polymer so-obtained may be activated and grafted to (conjugated with) a drug or an enzyme to alter the properties thereof.

6 Claims, 3 Drawing Sheets

NEW CHAIN-TERMINATED N-VINYL LACTAM POLYMERS AND GRAFT-COPOLYMERS AND METHODS FOR MAKING SAME

BACKGROUND OF THE INVENTION

1. Field of the Invention

The present invention relates to new, low molecular weight, chain-terminated, 5-membered-N-vinyl lactam polymers (oligomers), and more particularly to water-soluble, N-vinyl pyrrolidone polymers (oligomers) functionalized at one end with an hydroxyl, carboxyl or alkoxycarbonyl group; activated derivatives of such compounds and graft copolymers (or conjugates) thereof with drugs and enzymes; and the methods for preparing such products. Chain termination is effected by polymerizing the N-vinyl monomer in an isopropoxy-containing solvent as the chain terminating agent. For grafting the polymer to drugs and enzymes it is most preferable to convert functional moiety (e.g. —OH, —COOH, or —COO ($C_1$, to alkyl)) to a more "reactive" group for effective grafting or conjugation to the drug or enzyme. Exemplary reagents for this activation include carbonyl di-imidazole, dicyclohexylcarbodiimide (DCC), p-nitrophenyl-chloroformate, 2,2,2,-trifluoroethane sulfonyl chloride, etc.

2. Description of the Prior Art

The availability of amphiphilic oligomers or low molecular weight polymers exhibiting a variety of structures and properties, properly functionalized at the end of the polymer so as to permit the bonding of biological compounds is of great interest inasmuch as it allows the chemical, physical, and pharmacological properties of such biological compounds to be modified. Such polymers find their application in modifications of polypeptides and enzymes (A. Abuchowski and F. F. Davis, "Enzymes as Drugs", J. S. Holcenberg and J. Roberts, Ed., Wiley & Sons, pages 367–384, (1981); F. M. Veronese, Chimica Oggi, pages 53–56, Jan.–Feb. (1989)), and also can be applied in the preparation of "Pro-Drugs" (P. Ferruti and E. Ranucci in "High Performance Biomaterials", M. Szycher, Ed., Technomics Publ., Inc., pages 539–572 (1991)), and in the surface modification of biomaterials.

The modification of enzymes with amphiphilic polymers can, on the one hand, extend their application as biocatalysts in organic solvents, and on the other hand allow for a wider pharmaceutical use of enzymes and polypeptides. It has been observed, in fact, that derivatized enzymes will stay longer in the blood as a result of the combined effects of reduced ultrafiltration and degradation by proteases, diminished immunological reactions, and furthermore may present new targets in the organism.

It has previously been proposed by one of the co-inventors herein to produce low molecular weight N-vinyl pyrrolidone polymers with chain terminating hydroxy and carboxy groups utilizing mercaptoethanol and mercaptoacids, particularly mercaptoacetic acid as the chain-terminating compounds, and reacting same with polysaccharides, and in particular, dextrans to produce a graft copolymer of N-vinyl pyrrolidone and dextran. [F. M. Veronese, L. Sartore, P. Caliceti, O. Schiavon, E. Renucci and P. Ferruti, J. Bioact. and Compat., Vol. 5, pages 167–178 (1990).]

Other techniques which have ben tried include 1) a partial hydrolysis of the lactam rings in the polymer chain leading to the formation along the chain of carboxylic groups, and 2) copolymerization of N-vinyl pyrrolidone with small quantities of functional comonomers such as acrylic acid. The latter two methods lead to multifunctional products, which is not acceptable. Chain termination with mercaptoalcohols and mercaptoacids has not satisfactorily produced the one-end functional oligomers inasmuch as the transfer constant of the mercaptans in the polymerization of the N-vinyl pyrrolidone moiety is very high, and therefore this method results in poorly reproducible products containing large quantities of non-functional polymers of high molecular weight, and only small quantities of the more desirable low molecular weight functional polymers (oligomers).

BRIEF DESCRIPTION OF THE DRAWING FIGURES

DESCRIPTION OF THE INVENTION

Figure 1A:
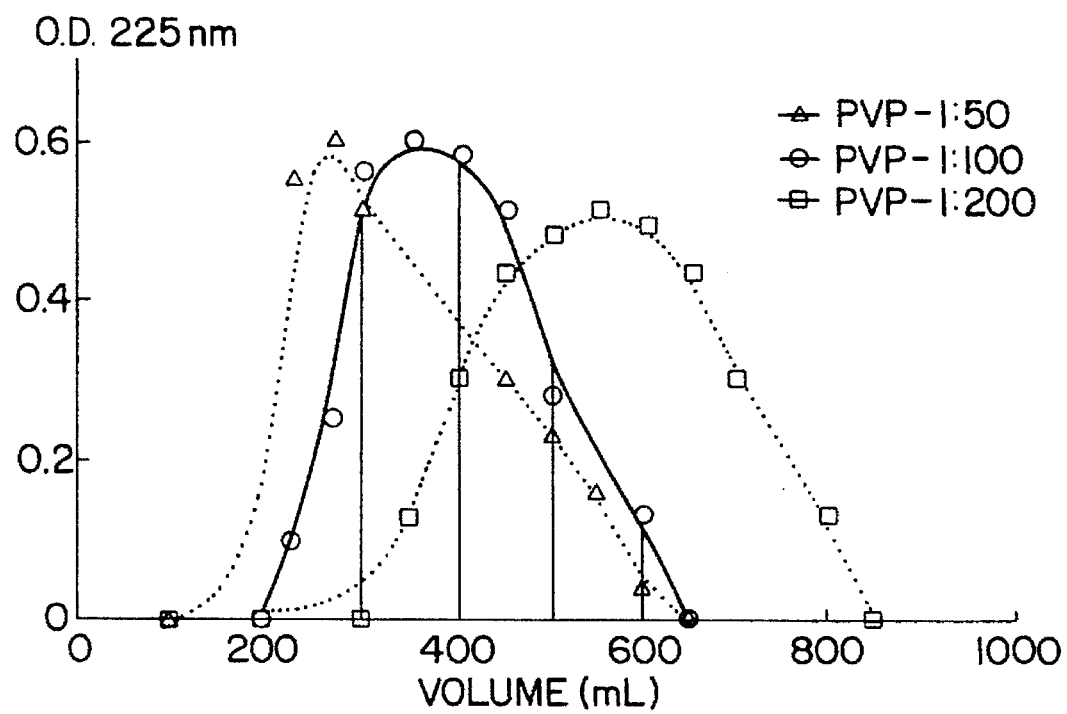
FIG. 1A is an elution profile using gel permeation chromatography for polyvinylpyrrolidone (PVP) synthesized using varying ratios of N-vinyl pyrrolidone to isopropoxyethanol (i.e. 1:50, 1:100 and 1:200).

A method for the production of functional low-molecular weight polymers (oligomers) of N-vinyl lactams and in particular, of N-vinyl pyrrolidone has been developed which involves the oligomerization of the N-vinyl lactam monomer in a solution of an isoalcohol, isoalcohol acid or isoalcohol ester, the latter serving both as a solvent and chain-terminating agent, e.g., isopropoxy alcohols, isopropoxy acids or isopropoxy acid esters. Suitable compounds have the following structures:

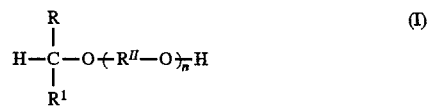

and

wherein R and $R^I$ are $C_1$ to $C_4$ alkyl or substituted alkyl; n is 0 to 20; $R^{II}$ is ethylene; $R^{III}$ is $C_1$ to $C_{24}$ alkylene or substituted alkylene; and $R^{IV}$ is $C_1$ to $C_4$ alkyl or substituted alkyl or hydrogen.

The polymerization (i.e. oligomerization) reaction is effected using, preferably, a free radical polymerization catalyst. Suitable catalysts (i.e. initiators) include peroxides and azo nitrogen compounds such as benzoyl peroxide, p-tertiary butyl peroxide, hydrogen peroxide, azobis-isobutyronitrile (AIBN) and the like. It is preferred to carry out the oligomerization, whether batch or continuous, in an inert atmosphere (e.g., nitrogen). A continuous process is preferred when the narrowest molecular weight distributions are desired. The reaction time may vary from minutes to several hours (e.g., 2, 3, 4, 6, 10, 12, 20, etc. hours) depending on temperature, catalyst concentration, and whether the polymerization is a continuous or batch process. The amount of catalyst may vary from about 0.01% to several percent (e.g., 1.0, 2.0, 2.5, up to about 5%) by weight, based on monomer weight. A preferred range is 0.01% to about 2% and, more preferably, a range of about 0.5% to about 1.5%.

The polymerization process is generally conducted at moderate temperatures ranging from about 0° C. to 120° C., preferably 0° C. to 100° C. or from ambient temperatures (e.g., 15°or 20° C.) to 50°, 60°, 70° or 80° C.

The amount of chain terminator-solvent compounds may vary, depending on the polymer molecular weight, from abut 1 part of the chain transfer agent up to about 300 parts of the chain transfer agent. During the polymerization, a chain transfer reaction takes place which involves the extraction of the hydrogen atom linked to the tertiary carbon atom, a process which initiates a new polymer chain. The global transfer constant ($C_{tr}$) is defined as the ratio between the constants relative to the transfer reaction, $K_{tr}$, and the polymerization constant, $K_p$; this is expressed as $C_{tr}=K_{tr}/K_p$, which equals approximately $1\times10^{-4}$. Preferred ratios of monomer to chain transfer agent range from bout 1:20 to about 1:200, with more preferred ratios ranging from about 1:25 to about 1:150. Illustrative preferred ratios are 1:50 and 1:100.

The polymerization products are isolated by known techniques; for example, the solvent may be partially or totally removed by distillation, preferably under vacuum. The crude material can be conveniently isolated by dilution with an appropriate solvent, for example, diethyl ether.

Where desirable and/or necessary for further utilization of the oligomerized products for effecting the graft (conjugation) with drugs and enzymes, the polymer product is processed to produce one with a low level of polydispersion (i.e. high level of narrow molecular weight distribution and one-end mono-functionality). Among the techniques for achieving this are gel permeation chromatography and precipitation with organic solvents. An illustrative, preferred fraction has a molecular weight of about 6,000.

The products of the oligomerization of the N-vinyl lactams conform to the following general formulas:

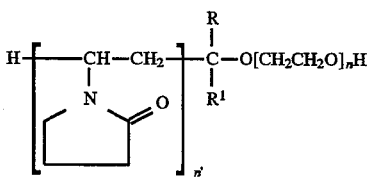

(III)

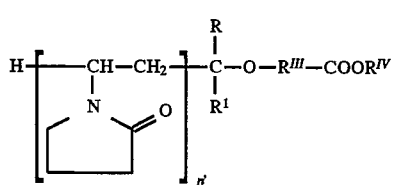

(IV)

wherein.

n' ranges from about 8 to about 180;

R and $R^I$ are $C_1$ to $C_4$ alkyl or substituted alkyl;

$R^{III}$ is $C_1$ to $C_{24}$ alkylene or substituted alkylene; and $R^{IV}$ is hydrogen or $C_1$ to $C_4$ alkyl or substituted alkyl.

In order to effect the reaction between the lactam polymer and the drug or enzyme, it is highly desirable to "activate" the chain-ended polymer. Preferred activators include N,N-carbonyldiimidazole, dicyclohexylcarbodiimide, 4-nitrophenylchloroformate, 2,2,2-trifluoroethanesulfonyl chloride, N-hydroxysuccinimide, and the like.

The use of the foregoing activators results in the provision of terminal groups on the lactam polymer which facilitate the reaction of grafting or conjugating to the drugs and enzymes contemplated herein. In the case of the hydroxy-terminated lactam polymers, one can produce either carbonate or carboxylic acid esters as the reactive moiety, and in the case of carboxyl terminated lactam polymers, reactive esters of the lactam polymer are readily formed.

The procedure for carrying out the activation reactions is generally conducted under anhydrous conditions using chlorinated organic solvents such as chloroform and methylene chloride. The procedure is conventionally conducted at moderate temperatures (e.g., the introduction of a solution of the activator dropwise into the anhydrous solution of the polymer at about 0° C., and, over a period of several hours (e.g., 1, 2, 3, 4, etc. hours) while raising the temperature to ambient (room) temperature). Continuous stirring during the entire procedure is conventional. The amount of the activator compound should, at the very minimum, be present in equimolar amounts relative to the chain-terminated polymer. Preferably, the activator should be present in molar excess, e.g., 1.2, 1.5, 1.8, 2, 3 and more moles per mole of chain-terminated lactam polymer.

While the chain transfer agents useful herein can be used to provide carboxy-terminated oligomers, it is also viable, as an alternative procedure, to effect terminal carboxyl moieties on the hydroxy-terminated oligomers by reacting the latter with an amino acid such as glycine, tryptophane, norleucine and/or a peptide and thereafter derivatizing (i.e. "activating") such as by the use of N-hydroxysuccimide. As a further alternative, the oligomer's terminal hydroxy group can be converted to a carboxy one by means of a reaction with a dicarboxylic anhydride such as succinic anhydride and then activated with N-hydroxysuccinimide.

The preparation of grafts or conjugates of the activated oligomers and the drugs or enzymes is carried out under moderate conditions of temperature e.g., 0° to 100° C., preferably, at or near ambient temperatures (e.g., 10° C., 20° C., 30° C., 40° C., etc.), generally for several hours (e.g., 1, 2, 3, 4, 5, 6, 7, 8, 10, etc. hours) with stirring. Isolation of the desired final product is done by the usual and conventional techniques.

Any enzyme or drug may be modified in accordance with the present invention. Illustrative enzymes and drugs include Superoxide Dismutase (SOD), doxorubicin, ampicillin, amoxicillin, and the like.

The relative quantities of activated oligomer and the biological (e.g., drug or enzyme) will obviously vary depending on the degree of modification by the oligomer, the reaction conditions and the like. Typically, the molar ratio of protein $NH_2$ groups to activated polymer may vary from about 1:1 to about 1:10 and, in the case of non-proteins to oligomer, from about 10:1 to about 1:10, with 5:1 to 1:5 preferred and 3:1 to 1:1 more preferred.

The following examples will serve to illustrate the present invention. Parts are by weight unless otherwise indicated.

EXAMPLE 1

10 grams of N-vinylpyrrolidone are dissolved in 500 ml of isopropoxyethanol and 200 mg of AIBN (azobisisobutyronitrile), freshly re-crystallized, is added to the mixture which is placed under successive stages of vacuum and nitrogen flushing to eliminate all traces of oxygen from the system. The mixture is held for 12 hours at 60° C., concentrated to a small volume and the product precipitated by successive additions of ethyl ether and then desiccated at 40° C. up to a constant weight. Yield is 95%, intrinsic viscosity [η]=0.03 dl/g.

EXAMPLE 2

By maintaining, unchanged, all the experimental reaction procedures of Example 1, and varying the ratio between the monomer and isopropoxyethanol (1/100 respectively), one obtains a product with [η]=0.04 dl/g and a yield of 93%.

EXAMPLE 3

Polymer Fractionation Through Gel Chromatography of PVP-C(CH$_3$)$_2$OHC$_2$CH$_2$OH (PVP-OH)

Figure 1B:
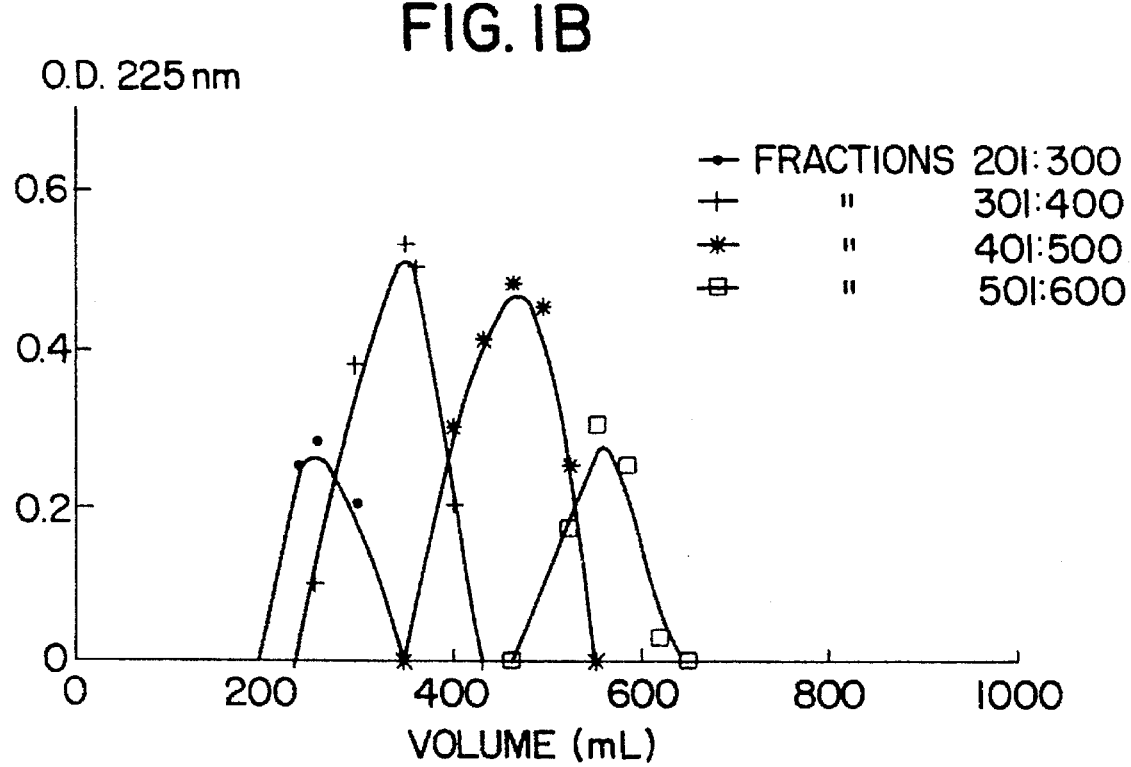
FIG. 1B is an elution profile of 4 fractions of the PVP— 1:100 material in the gel permeation chromatography procedure.

The oligomerized vinyl pyrrolidone synthesized in isopropoxyethanol (ratio of 1:100) and with an intrinsic viscosity [η] of 0.03 dl/g, is fractionated using Bio Gel P100 gel chromatography. A 1.1 g sample is dissolved in 3 ml of water and stirred for 1 hour, placed in a column (diameter =5 cm, height =50 cm) and eluted with double-distilled water. The eluate is assayed with iodine (G. E. C. Sims and T. J. Snape, Anal. Biochem., 107, 60–63 (1980)) and measured at 225 nanometers (nm) for optical density (O.D.). The end product is fractionated into Four fractions which are collected and then lyophilized separately. In FIG. 1A, the solid curve shows the elution profile of the 1:100 product and the four fractions collected, i.e. fraction 1 from 201 to 300 ml; fraction 2 from 301 to 400 ml; fraction 3 from 401 to 500 ml; fraction 4 from 501 to 600 ml. FIG. 1B shows the elution profile in the same column of each of the four fractions. The dotted curves in FIG. 1A illustrate the elution profiles of oligomers prepared at monomer/chain terminator alcohol rations of 1:50 (dotted curve with a points) and 1:200 (dotted curve with □ points).

The following Table shows the amount of lactam polymer recovered in the 4 fractions of FIG. 1B and their corresponding molecular weight (MW) as determined by osmometry.

TABLE 1

| FRACTION | WEIGHT RECOVERED (mg) | MW (by osmometry) |
| --- | --- | --- |
| 1 | 100 | 16,00 |
| 2 | 260 | 9,500 |
| 3 | 240 | 5,500 |
| 4 | 140 | 3,200 |

EXAMPLE 4

Polymer Fractionation through Fractional Precipitation

The fractionation of the polymer (Ex. 3) is also done by using isopropanol/ether precipitation according to the following methodology: 20 g of PVP-OH in 200 ml of isopropanol are precipitated through successive additions of ethyl ether in the ratios shown in Table 2. The precipitate obtained after each addition of ether is filtered, recovered with a small amount of CH$_2$Cl$_2$ and precipitated again in ether. Table 2 also shows the quantity of polymer recovered with each fraction, and for fractions 2, 3 and 4, the molecular weight calculated by osmometry.

Figure 2:
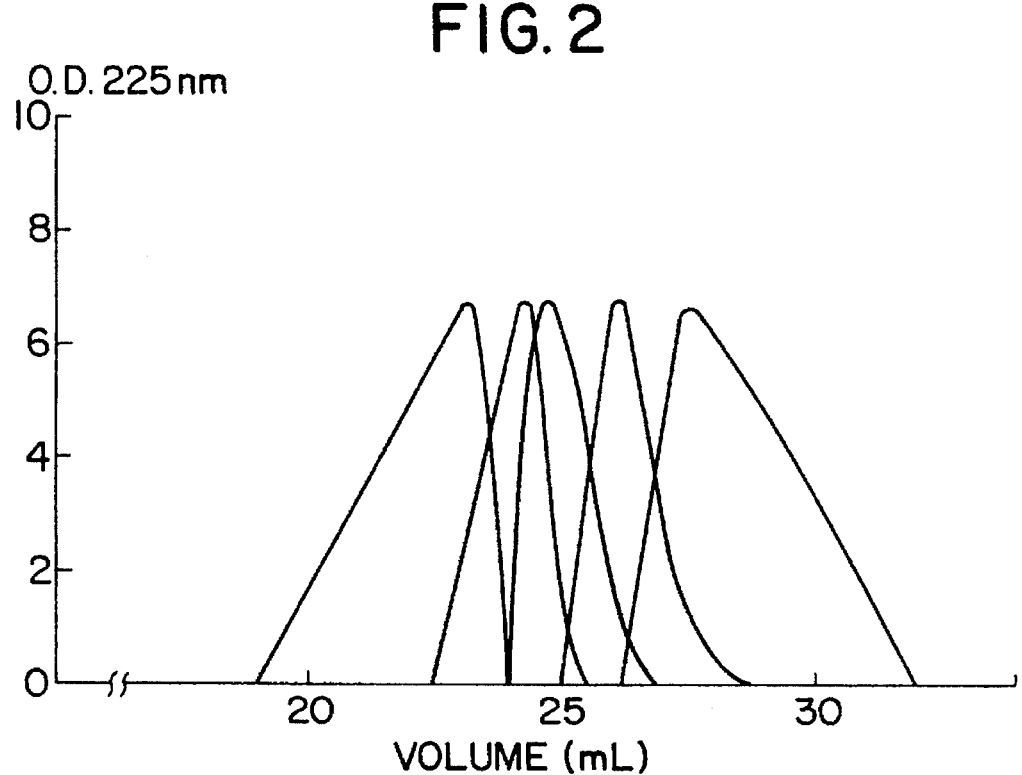
FIG. 2 is the elution profile of 5 fractions of the PVP— 1:100 material in the isopropanol/ether precipitation according to Example 4.

The fractionation process is verified through analytic chromatography using a permeation gel column (Bio Gel SEC 30 XL) operating in an HPLC system. FIG. 2 shows the elutions of the fraction samples 1–5 from Table 2, confirming the various molecular weights and the homogeneity of each single fraction.

TABLE 2

FRACTIONATION BY PRECIPITATION WITH SOLVENTS; RECOVERED QUANTITY; VOLUME OF ETHER USED AND OSMOMETRIC MOLECULAR WEIGHT

| FRACTION | RECOVERED WEIGHT (g) | VOLUME Et$_2$O | MW |
| --- | --- | --- | --- |
| 1 | 8.25 | 1,200 | — |
| 2 | 4.88 | 300 | 6,000 |
| 3 | 1.85 | 300 | 3,450 |
| 4 | 1.42 | 400 | 2,450 |
| 5 | 0.6 | 200 | — |
| 6 | 2.2 (oil) | — | — |

A preferred fraction for producing drug and enzymatic derivatives is the one with a mean molecular weight of about 6,000, which corresponds to Fraction 2 (Table 2) and to Fraction 3 in Table 1 (permeation gel fractionation).

The following examples illustrate "activation" reactions of the oligomer obtained through the fractionated precipitation method.

EXAMPLE 5

Activation with "TFES"

1.2 g of polymer (Fraction 2, Table 2, 0.2 mM) is dissolved in a minimum quantity of anhydrous CHCl$_3$ and is further dehydrated with CaH$_2$. To the anhydrous solution which is cooled in an ice bath, is added (under stirring) a slow drip of 130 ul (1.2 mM) of pyridine and 120 uL (1 mM) of 2,2,2-trifluoroethane sulfonyl chloride (TFES). The mixture is raised to room temperature, with stirring, for 2 hours. The reaction product is precipitated in ethyl ether, filtered, dissolved with CH$_2$Cl$_2$ and precipitated again in ethyl ether. The reprecipitation process is repeated until all traces of pyridine are eliminated; the latter is determined by UV absorption (λ max 255 nm). 1.1 g of product are obtained, with a 90% yield.

EXAMPLE 6

Activation with Carbonyl Diimidazole 1.2 g of polymer (Fraction 2, Table 2, 0.2 mM) are dissolved with a minimum amount of anhydrous chloroform and further dehydrated with calcium hydride. 98 mg (0.6 mM) of carbonyl diimidazole are added to the solution and the resulting mixture stirred for 30 minutes. The activated polymer is then precipitated with ether and recrystallized a few more times with methylene dichloride/diethyl ether. 1.15 g of product are obtained, with a yield of 93%.

EXAMPLE 7

Activation with P-Nitrophenylchloroformate 1.2 g of polymer (Fraction 2, Table 2, 0.2 mM) are dissolved with a minimum amount of anhydrous chloroform and is further dehydrated with calcium hydride. 81 mg (0.4 mM) of p-nitrophenylchloroformate and triethylamine are added to the solution until the pH reaches a value of 8. The reactive mixture is kept under dark, at room temperature and stirred overnight; the mixture is then dripped into a solution of ethyl ether, while stirring. The resulting precipitate is then filtered, desiccated with $P_2O_5$ and recrystallized with $CH_2Cl_2/(C_2H_5)_2O$. 1.2 g of product are obtained, with a yield of 97%.

EXAMPLE 8A—Part I

Aminoacid Coupling to The Activated Carbonate of Example 7 and Carboxy Activation at the γ Location as A Succinimidyl Ester 1.25 g (0.2 mM) of the p-nitrophenylcarbonate (prepared according to Example 7, above) is added to 1 millimole of glycine, dissolved in 10 ml of 0.2 borate buffer and brought to pH 8 over a period of 3 hours, under stirring; the pH should be maintained in the range of 8–8.3 with NaOH (0.1N). The mixture is maintained under stirring for 8 hours, after which it is cooled in an ice bath and the pH is brought down to 3 with HCl (2N). The byproduct of this reaction, paranitrophenol, is extracted two times with ethyl ether, whilst the aqueous phase is concentrated down to a volume of 3 ml. (This product eliminates all excess aminoacid by precipitation.)

The product is finally purified from any unbound aminoacid by chromatographic means in a Bio Gel P 60 column (d=5 cm, h=50 cm). The fractions containing PVP-aminoacid-OH are collected and dry-concentrated. 0.9 g of product are obtained, with a yield of 72%.

The functionality of the product is approximately 40%, calculated by potentiometric titration of the carboxyl group, analysis of the aminoacid following acid hydrolysis and spectrophotometric determination.

EXAMPLE 8A—PART II 0.9 g (0.15 mM) of PVP-aminoacid-OH (product of Example 8A, Part I) are dissolved in a minimum amount of anhydrous $CH_2Cl_2$ and cooled in an ice bath. 35 mg (0.3 mM) of N-hydroxysuccinamide are added, followed by 62 mg (0.3 mM) of dicyclohexylcarbodiimide. The mixture is brought back to room temperature and then stirred for 4 hours. The dicyclohexylurea is eliminated by filtration whilst the PVP-aminoacid-OSu (succinimidyl ester) is precipitated in ethyl ether and then recrystallized with $CH_2Cl_2$ ethyl ether, obtaining 0.9 mg with a yield of 98%.

EXAMPLES 8B and 8C

Example 8A, Parts I and II, is repeated using tryptophane (8B) on the one hand and norleucine (8C) on the other hand, in place of glycine.

EXAMPLE 9

Conversion with Succinic Anhydride and Activation with N-hydroxy-succinimide

Dissolve 1.2 g of polymer (Fraction 2, Table 2, 0.2 mM) in a minimum quantity of $CHCl_3$ and further dehydrate with $CaH_2$. The anhydrous solution is heated to 60° C., and 40 mg (0.4M) of succinic anhydride and 35 uL (0.4 mM) of pyridine are added as catalysts. The mixture is kept overnight under stirring and the product is then isolated by precipitation in ether. It is then precipitated with $CH_2Cl_2$/ethyl ether, obtaining 1.1 g of product (monosuccinate) with a yield of 98%. The "free" carboxyl activation is done following the procedure described in Example 8 by means of succinimidyl ester.

EXAMPLE 10

SOD Modification 2 mg of SOD is dissolved in 1 ml of borate buffer (0.2M; pH 8) and then 40 mg of activated polymer is added while stirring vigorously (protein $NH_2$: polymer (molar ratio)= 1:5). The resulting mixture is agitated for 6 hours and purified from any reaction impurities and from excess polymer by means of ultrafiltration with an Amicon system using a PM 10 membrane, followed by molecular exclusion chromatography with a Superose 12 TM column eluted with a $NaH_2PO_4/NaCl$ buffer in FPLC (Pharmacia). The protein concentration of the purified product is determined by means of biuret assay. (A. G., Gornall, C. J. Baldwell & David, J., Biol. 101 Chem. 177, pp. 651 (1949)), the residual activity is evaluated by enzymatic activity (F. Paoletti, D. Aldinucci, A. Mocali and A. Caparrini, Anal. Biochem. 154, pp. 536–541 (1986)) and finally the number of polymeric chains bonded to an enzyme molecule is determined by the Habeeb assay (A.F.S.A. Habeeb, Anal. Biochem. 14, pp. 328–336 (1966)).

In the case of the norleucine conjugate (graft) prepared from the Example 8C activated oligomer, the degree of modification is also determined by amino acid analysis.

Thus, Example 10 is carried out with six different activated polymers using the activated oligomers of Examples 5, 6, 7, 8B and 8C. The following Table 3 shows the data for the degree of PVP functionalization of the enzymes (expressed as a percentage of amino groups with PVP linkage) obtained by means of the 4 methods exemplified herein, and the percentage of residual activity for the modified enzyme.

TABLE 3

| No. | Activated PVP | % Modification | % Residual Enzyme Activity |
|---|---|---|---|
| 1 | PVP-O—$SO_2$—$CH_2$—$CF_3$ (Ex. 5) | 15 | 90 |
| 2 | PVP-O—CO-IMIDAZ (Ex. 6) | 10 | 90 |
| 3 | PVP-OCO—O—$C_6H_4$—$NO_2$ (Ex. 7) | 40 | 85 |
| 4 | PVP-OCO-AA-OSU (Ex. 8C) | 25 | 85 |

Similar results are obtained varying reaction conditions (temperature, solvent systems, buffers, etc.) within the parameters disclosed herein.

EXAMPLE 11

Preparation of PVP-SOD Labeled with Tritium 10 mg of PVP-SOD, expressed in protein weight (prepared using the activated PVP No. 1 of Table 3, above), was dissolved with 1 ml of borate buffer (0.2M, pH 8) to which is added, under vigorous stirring, 0.5 mg of N-succinimidyl propionate, labeled with 3 (NSP 130,000, 000 dpm/mg). The ratio of free amino groups to the N-succinimidyl propionate is 1:0.5 Part of the protein's free amino groups became activated with the radioactive propionate. The modified and labeled enzyme is purified by ultrafiltration in an Amicon cell with a PM 10 membrane until any free propionate is entirely eliminated, and the hydroxysuccinamide is chromatographed as described in Example 10. The product as thus obtained exhibits a protein radioactivity of 910,000 dpm/mg.

EXAMPLE 12

PVP-SOD Clearance in Rats

Figure 3:
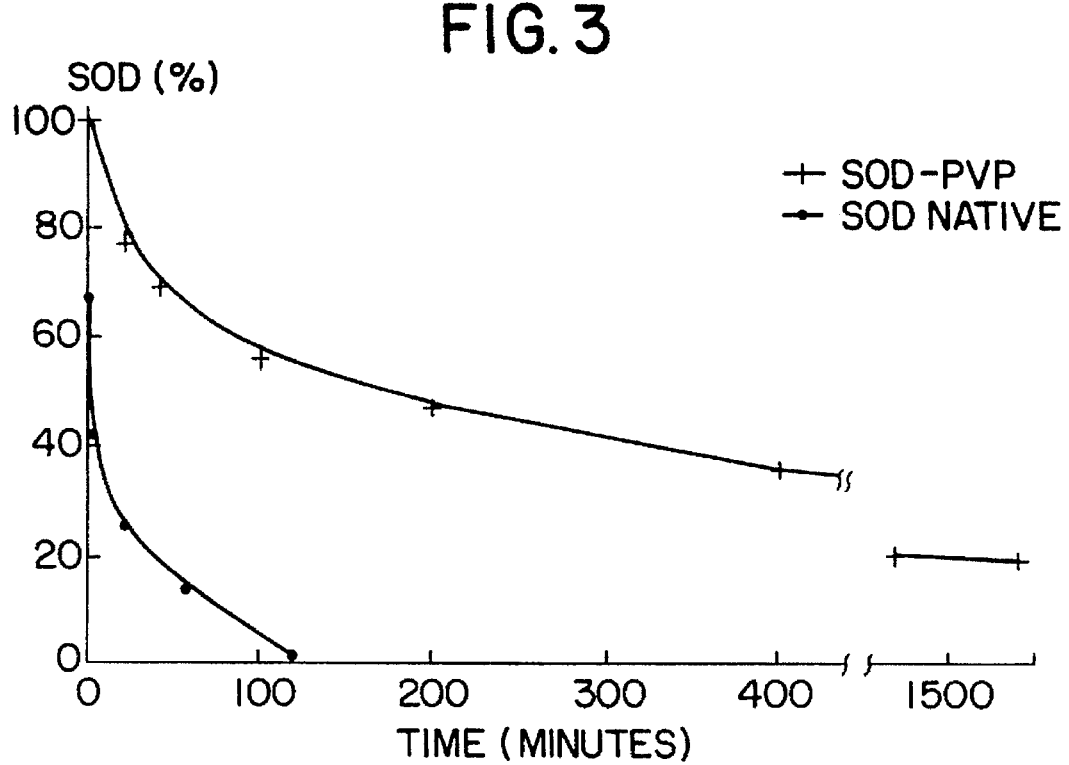
FIG. 3 is a pharmacokinetic profile of SOD and SOD-PVP, intravenous in rats, showing the percent of enzyme in plasma as a function of time, from Example 12.

Dissolve 1 mg of native SOD, labeled with radioactive N-succinimidyl propionate, as described in Example 11, above, and 1 mg of PVP-SOD in protein form (as utilized in Example 11) (910,000 dpm/mg) with 0.5 ml of 10 mM, $Na_2HPO_4/NaH_2PO_4$, 0.15M NaCl, pH 7.2, buffer. The solutions of the native of derivatized PVP-enzyme are injected into the caudal vein of male Wistar rats, fed "ad libitum", and weighing 200 g. Blood samples are drawn from their hearts at established times with heparinized syringes. The radioactive count is performed on samples of 100 uL of plasma obtained by centrifugation of the blood samples. The radioactive values are expressed as a percentage of the value obtained 1 minute after injection, graphically plotted as a time function. FIG. 3 shows the elimination profile of both the PVP-SOD and the native SOD. The T ½ value is 6' for native SOD and 210' for PVP-SOD, whilst the T10% is 720' for PVP-SOD and 70' for native SOD.

EXAMPLE 13

PVP-SOD Antigenicity

Figure 4:
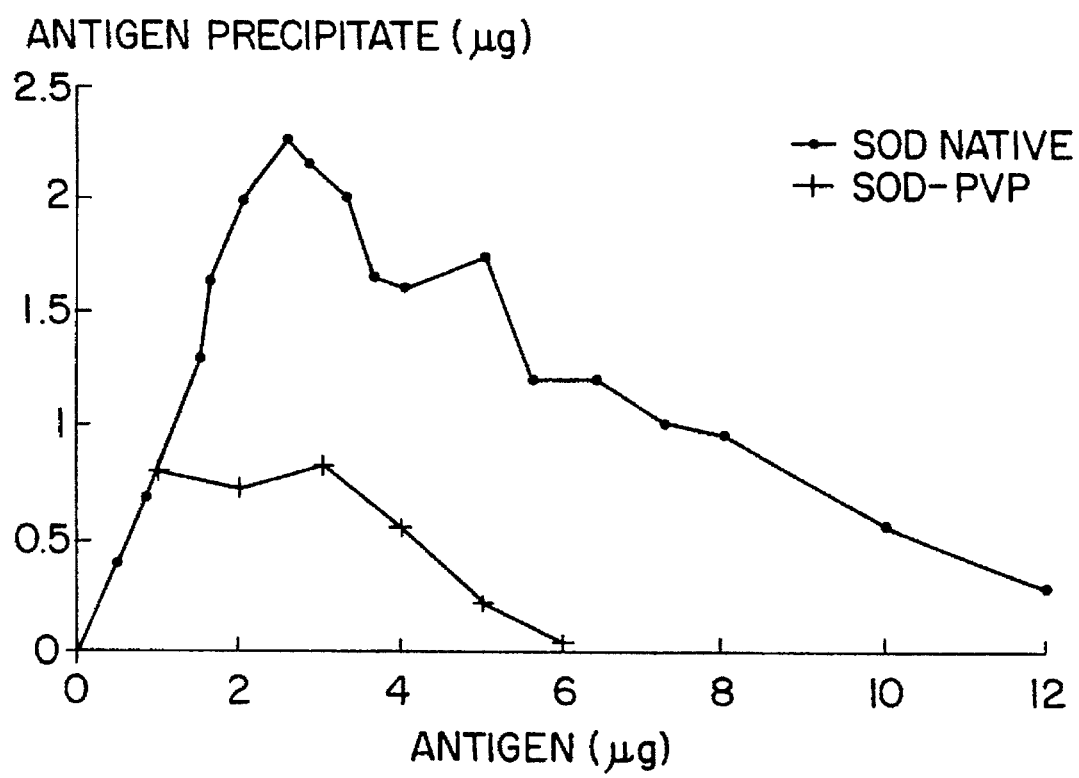
FIG. 4 is an immunoprecipitation profile of rabbit antiserum immunized against native SOD as obtained for native SOD and SOD-PVP, in Example 13.

To 90 uL of rabbit anti-serum immunized against native SOD is added an aliquot of 0 to 60 uL (of 0.2 mg/ml protein) of native SOD (640,000 dpm/mg) or PVP-SOD, prepared as in Example 11 (580,000 dpm/mg) in a 10 uM TRIS-HCl/0.15M NaCl pH 7.4 buffer. The final volume is brought to 150 uL with the TRIS/NaCl buffer. The samples are incubated for 30 minutes at room temperature, at 4° C. for 20 hours and then centrifuged for 15 minutes at 5000 rpm. The resulting precipitate is washed 3 times with 800 uL of the TRIS/NaCl buffer and finally solubilized with 300 uL of NaOH 0.1N. The radioactive counting is performed on a 100 uL sample. The results shown, in FIG. 4 demonstrate the decreased antigenicity of the PVP-SOD compared to the native enzyme.

EXAMPLE 14

Oligomer-Drug Conjugates a) PVP-Doxorubicin 120 mg of doxorubicin (0.2 mM) are dissolved in 3 ml of dimethyl sulfoxide (DMSO) and added with 600 mg (0.1 mM) of PVP-0-CO-O-$C_6H_4NO_2$ (prepared as in Example 7) dissolved in 10 ml of anhydrous $CH_2Cl_2$.

The mixture is brought to a pH of 8 with triethyl amine (TEA) and after undergoing overnight stirring at room temperature, it is dripped into ether, under stirring. All the oligomeric specimens starting from a PVP-drug combination are precipitated using this procedure.

The precipitate is slowly dissolved in 2 ml of aqueous solution (pH 8) containing 1 mM of the drug and the pH 8–8.3 is maintained with NaOH 0.2N. The mixture is kept at room temperature and stirred for 8 hours; thereafter the oligomer-drug is purified from impurities by means of exclusion chromatography with a Bio Gel P 60 resin column (d=3 cm, h=30cm) and finally eluted with $Na_2HPO_4/NaH_2PO_4$ (0.15M, pH 7). The eluate is assayed by iodine to identify the polymer whilst the doxorubicin is identified by O.D. at 480 nm. The fractions containing the polymer drug conjugates are collected, and ultrafiltered several times in an Amicon cell with a YM 2 membrane to eliminate all remaining salts. The end product is then lyophilized. The percentage of PVP-OH (O.D. 480 nm) remaining in the PVP-drug end product is 31.2%.

b) PVP-Ampicillin

The PVP-ampicillin derivative is obtained following the same procedure in a), above. The percentage of PVP-drug conjugated relative to the total quantity of isolated product is 30.5%, determined by UV spectroscopy.

c) PVP-Amoxicillin

The PVP-amoxicillin derivative is obtained following the procedure described in a) above. The percentage of PVP-pharmaceutical relative to the total quantity of isolated product is 41%, determined by UV spectroscopy.

EXAMPLE 15

Example 1 is repeated using the following indicated component amounts.

| | Monomer | Chain-Terminator | Catalyst |
|---|---|---|---|
| 15a | NVP[1]-10 g | IPE[2] 800 ML | AIBN[3] 200 mg |
| b | NVP-10 g | IPMA[4] 1000 ML | AIBN 200 mg |
| c | NVP-10 g | IPMA 500 ML | TBP[5] 300 mg |
| d | NVP-10 g | IPPEG[6] 1000 ML | AIBN 200 mg |
| e | NVP-10 g | IPS[7] 1000 ML | TBHP[8] 200 mg |
| f | NVO[9]-10 g | IPE 1000 ML | AIBN 200 mg |

[1] NVP = N-vinyl pyrrolidone
[2] IPE = isopropoxyethanol
[3] AIBN = azobisisobutyronitrile
[4] IPMA = isopropoxymethylacetate
[5] TBP = ditertiarybutyl peroxide
[6] IPPEG = $(CH_3)_2CH-O-(CH_2CH_2O)_2OH$
[7] IPS = $(CH_3)_2CH-O-COCH_2CH_2COOH$
[8] TBHP = tertiarybutyl hydroperoxide
[9] NVO = N-vinyl-4-oxazolidinone

What is claimed is:

1. A water-soluble polymer consisting of a polyvinyl 5-membered lactam having a molecular weight ranging from about 1000 to about 20,000 and chain-terminated with a compound selected from the group consisting of compounds of the following formulas:

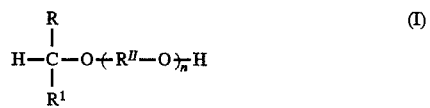

(I)

and

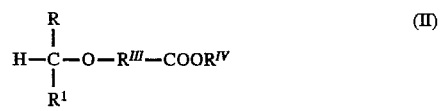

(II)

wherein R and $R^1$ are $C_1$ to $C_4$ alkyl or substituted alkyl; n is 1 to 20; $R^{II}$ is ethylene; $R^{III}$ is $C_1$ to $C_{24}$ alkylene or substituted alkylene; and $R^{IV}$ is $C_1$ to $C_4$ alkyl or substituted alkyl.

2. A polymer as defined in claim 1 wherein the chain-terminating compound is a formula (I) compound.

3. A polymer as defined in claim 2 wherein the chain-terminating compound is isopropoxyethanol.

4. A polymer as defined in claim 3 wherein the molecular weight is about 6000.

5. A polymer as defined in claim 1 wherein the chain-terminating compound is a formula II compound.

6. A polymer as defined in claim 5 wherein the chain-terminating compound is isopropoxymethyl acetate.

* * * * *